(12) United States Patent
Eisenberg et al.

(10) Patent No.: US 7,441,899 B2
(45) Date of Patent: Oct. 28, 2008

(54) PANRETINAL LASER FUNDUS CONTACT LENS

(76) Inventors: Elliot S. Eisenberg, 1215 Greenwich #4A, San Francisco, CA (US) 94109; Tony Partono, 347 Dolores St., San Francisco, CA (US) 94110

( * ) Notice: Subject to any disclaimer, the term of this patent is extended or adjusted under 35 U.S.C. 154(b) by 187 days.

(21) Appl. No.: 11/650,081

(22) Filed: Jan. 5, 2007

(65) Prior Publication Data
US 2008/0165323 A1 Jul. 10, 2008

(51) Int. Cl.
*A61B 3/00* (2006.01)
*A61B 18/18* (2006.01)

(52) U.S. Cl. .................. 351/219; 351/205; 351/246; 606/4

(58) Field of Classification Search .................. 351/219, 351/220, 221, 205, 246; 606/4, 6; 600/476
See application file for complete search history.

(56) References Cited

U.S. PATENT DOCUMENTS

| | | | | | |
|---|---|---|---|---|---|
| 3,820,879 | A | * | 6/1974 | Frisen | 351/219 |
| 4,134,647 | A | * | 1/1979 | Ramos-Caldera | 351/219 |
| 4,506,962 | A | * | 3/1985 | Roussel | 351/160 R |
| 4,558,698 | A | * | 12/1985 | O'Dell | 606/6 |
| 4,568,157 | A | * | 2/1986 | Kurwa | 351/160 R |
| 4,598,984 | A | * | 7/1986 | Rol | 351/219 |
| 4,648,400 | A | * | 3/1987 | Schneider et al. | 606/3 |
| 4,966,452 | A | * | 10/1990 | Shields et al. | 351/219 |
| 5,141,506 | A | * | 8/1992 | York | 606/5 |
| 5,490,849 | A | * | 2/1996 | Smith | 606/5 |
| 5,548,352 | A | * | 8/1996 | Dewey | 351/160 H |
| 5,921,981 | A | | 7/1999 | Bahmanyar | |
| 6,066,128 | A | | 5/2000 | Bahmanyar | |
| 7,125,119 | B2 | * | 10/2006 | Farberov | 351/219 |
| 2005/0174538 | A1 | * | 8/2005 | Eisenberg | 351/219 |

OTHER PUBLICATIONS

U.S. Appl. No. 11/193,735, filed Jul. 29, 2005, Eisenberg/Partono.
U.S. Appl. No. 11/523,437, filed Sep. 19, 2006, Eisenberg/Partono.
U.S. Appl. No. 11/024,308, filed Dec. 28, 2004, Eisenberg.

\* cited by examiner

*Primary Examiner*—Ricky L Mack
*Assistant Examiner*—James R Greece

(57) ABSTRACT

An optical lens system is designed to speed and improve therapeutic laser irradiation of the inner eye. The device is housed in an external casing (10) in conjunction with a specialized fundus contact lens (22). Internally, a disc (12) is mounted with a rotary central mirror driven by a micromotor (14). Toward the periphery of the plate a ring of mirrors is arranged (20). Below the mounted disc lies an additional set of mirrors (24) set at inclinations to divert incident energy to the posterior segment of the eye. As incoming laser energy (28) strikes the central mirror it diverts the beam to a peripheral mirror which again deflects the light to another mirror at the posterior end of the device. A control box (30) facilitates coordinating laser bursts with the circumferential motion of the central mirror. The apparatus results in a ring of laser delivered to the internal eye.

11 Claims, 4 Drawing Sheets

PANRETINAL LASER FUNDUS CONTACT LENS

CROSS-REFERENCE TO RELATED APPLICATIONS

This application is related to application Ser. No. 11/024,308, filed Dec. 28, 2004 by one of the present inventors and Ser. No. 11/193,735, filed Jul. 29, 2005 and Ser. No. 11/523,437, filed Sep. 19, 2006 by both of the current inventors.

FEDERALLY SPONSORED RESEARCH

Not applicable

SEQUENCE LISTING OR PROGRAM

Not applicable

BACKGROUND OF THE INVENTION—FIELD OF THE INVENTION

The present invention relates to ophthalmic devices which assist in delivering laser therapy to the eye.

BACKGROUND OF THE INVENTION—PRIOR ART

The worldwide diabetic epidemic is a common cause of visual loss. In the United States prevalence estimates among patients with diabetes reveal approximately 40% show some degree of retinopathy. For severe diabetic retinopathy the incidence is at least 8% and probably higher. Diabetic retinopathy leads the way in causing legal blindness for adults 20-74 years of age. Annually there are 12,000-24,000 new cases diagnosed. Furthermore, the degree and severity of retinal disease usually increases with time. From a global standpoint there are currently at least 171,000,000 patients with diabetes. In 2030 it is projected that 366,000,000 will carry the diagnosis.

Both Type I and Type II diabetes put patients at risk for debilitating retinal problems leading to visual loss. Although Type II is about 20 time more prevalent than Type I severe retinopathy appears in both forms. Significant loss of vision is often due to the proliferative manifestation of the illness. In this scenario abnormal new blood vessels, neovascularization, grow on the retinal or vitreous surface of the eye. Subsequent bleeding, leakage, and traction from these aberrant vascular channels damages the retinal tissue resulting in visual loss.

In the 1970's a large, randomized multicenter controlled trial demonstrated that the proliferative form (severe—stage 5) of diabetic retinopathy was ameliorated by laser therapy. The Diabetic Retinopathy Study (DRS) became the gold standard showing that panretinal laser photocoagulation could reduce visual loss 50-60% in the neovascular form of the disease. This type of treatment is also used in other eye conditions where abnormal vascular proliferation is evident. They would include neovascular glaucoma, central retinal vein occlusion, and branch retinal vein occlusion. In addition, physicians are given the latitude to treat severe non-proliferative diabetic retinopathy with panretinal laser photocoagulation (PRP) in special circumstances.

The three delivery methods currently used to deliver this treatment all require a high degree of operator dexterity. The slit lamp system requires an operator to manually hold a fundus contact lens on the patient's anesthetized eye, aim an attenuated laser beam shot by shot, and repetitively depress a foot pedal to activate the energy delivery. The indirect ophthalmoscopic format forces the treating surgeon to hand hold a condensing lens in front of the treated eye, align and tilt a headpiece used to direct the laser beam, and fire the spots via a foot switch. Finally, the endoprobe methodology requires an operating room setting and completion of a vitrectomy. In addition, the surgeon must hold the probe in the internal eye and aim it using an operating microscope with an attendant contact lens. While this modality does have a repeat mode for automated laser firing it still necessitates expert user coordination and an operating theatre.

Regardless of the delivery format a full complement of laser treatment (PRP) usually includes 1500-2000 applications placed in a modified checkerboard pattern inside the eye. Multiple patient visits are the norm for completing this treatment. Not uncommonly a full course of therapy will require 60 minutes of patient and physician time. Upon completion of the procedure a ring or donut configuration of laser treatment spots will cause chorio-retinal scarring that improves the clinical course of proliferative retinopathy.

The slit lamp biomicroscope is the most widely used modality for delivering panretinal laser photocoagulation. Mechanically, a laser emitting source is connected via a fiber optic cable to a biomicroscope. The examiner then places an external fundus contact lens on the patient's eye after topical anesthetic is applied. Using a micromanipulator on the slit lamp the surgeon can focus an attenuated laser on the patient's retinal surface. After setting the beam size, power, wavelength, and treatment duration the laser can be fired by activating a foot switch. Typically 500 micron diameter laser spots are placed on the retina—one at a time. Primary absorption of the laser energy is by the retinal pigment epithelial cells and the mechanism of action is by thermal heat transfer. Despite over 35 years of applying treatments in this fashion the exact cellular or chemical reaction that mediates the salutary clinical effect is unknown.

The current methods of performing panretinal laser photocoagulation have a number of disadvantages. First, the procedure is time consuming. It usually requires at least two and more often three office visits to complete a full course of therapy. Not uncommonly a full hour of physician and patient time is spent performing the operation. Second, it requires a significant degree of physician coordination and attention to expertly administer treatment. In most cases the examiner must not only carefully focus, aim, and manually trigger the laser but he/she must fire the shots one at a time. Outside of one expensive laser platform currently on the market there is little automation in the procedure. Third, on a regular basis the laser burns cause patient pain. This can necessitate stopping treatments frequently to let the patient rest, it can necessitate administering retrobulbar anesthesia (injecting a numbing agent through the lid behind the globe of the eye), and it can necessitate stabilizing the patient's eyelids or head to prevent untoward movements during therapy. Finally, the operation has a number of complications. Some of these, such as operator aiming errors, are related to fatigue in either the physician or patient.

A device that would speed up the procedure or reduce the heavy burden of user coordination would be desirable. Furthermore, an invention that would reduce patient pain would be most welcome for all parties. Prior inventions have attempted solving some of these objectives but most have either failed or become oppressively expensive. U.S. Pat. Nos. 6,066,128 and 5,921,981 to Bahmanyar et al. (2000) (1999) address the time burden issue of administering panretinal photocoagulation. Using an optical device to effectuate splitting a single laser into four beams the authors propose a multispot application of laser with each triggering shot. It follows that 500 applications of treatment might produce 2000 spots at the chorioretinal interface. While this methodology may have some merit in reducing treatment times it fails to address problems of user coordination, aiming errors, patient pain, and treatment complications. Their device would still need to be aimed and triggered one shot at a time. Their device might be more painful delivering four simultaneous applications instead of one. And, their device does not lessen the manual dexterity required to provide a full complement of treatment. Finally, panretinal laser complications such as visual field contraction, nyctalopia, and central visual loss are not addressed by their invention.

In another attempt to cut laser treatment times a California corporation, OptiMedica, has employed a pattern-scanning laser system. Named PASCAL, this method cuts treatment times by placing grids or arrays of burns on the patient's retina with a single triggered application. A twenty five or fifty six spot array can be chosen employing a semi-automated pattern generation display. The shots are delivered in sequence with short 532 nm laser pulses. While laudably cutting conventional treatment times this laser and software package is not likely to find ubiquitous world wide usage. The platform is expensive, large in size, and not easily mobile. It is expected to cost over $75,000/unit.

In U.S. patent application Ser. No. 11/193/735 Eisenberg and Partono (2005) addressed issues of diminishing treatment times, reducing complications, minimizing operator errors, and improving procedure comfort. Their invention acts as a laser beam diverter so that treatment light is placed in a circumferential pattern. The process of panretinal photocoagulation is not only automated by their invention but the cheaper cost of the device will allow for worldwide distribution. With U.S. patent application Ser. No. 11/523,437 the same inventors (Eisenberg and Partono) refined their approach to automating panretinal laser photocoagulation by advancing a device that was even cheaper to build and worked on a different mechanical principle. Interposed between the hardware of a laser delivery device and the patient's eye their instrument reflects and diverts laser energy by a system of mirrors or prisms. The net effect is to reduce patient therapy times, reduce operators aiming errors, reduce complications of treatment, and reduce patient pain. Furthermore, the invention is mobile, small, adaptable to most conventional laser machines, and relatively inexpensive. Nothing in the current application reduces the efficacy and the viability of the author's prior devices. However, in the current invention the process is further simplified, the manufacturing cost is reduced, and a new mechanical mechanism is introduced.

BACKGROUND OF THE INVENTION—OBJECTS AND ADVANTAGES

Thus, several objects and advantages of our invention are;
a) to provide a device that is highly mobile and portable;
b) to provide an instrument that makes the process of panretinal laser photocoagulation faster;
c) to provide a method of performing treatment which decreases operator aiming errors;
d) to provide an instrument that reduces the pain of PRP;
e) to provide a method that minimizes the complications of laser therapy;
f) to provide an article of manufacture that reduces the user coordination required to perform laser surgery;
g) to provide an adaptation that increases the safety of the procedure;
h) to provide an article of manufacture that automates the delivery of panretinal laser photocoagulation.

Further objects and advantages of our invention will become apparent from a consideration of the drawings and ensuing description.

SUMMARY

The current invention is a fundus contact lens device that will assist in automating panretinal laser photocoagulation. It consists of a body or external housing that is designed to be placed on an anesthetized eye. Internally, a disc with holes is mounted with highly reflective peripheral mirrors or prisms to redirect the pathway of laser treatment light. The center of the disc contains a moveable mirror controlled by a micromotor. Rotation of the central reflecting device diverts light to peripheral mirrors which subsequently redirect the treatment beams. A ring of aligned mirrors or prisms at the bottom of the instrument captures the redirected laser energy and deflects it into the internal eye. The invention is regulated via a cable or remotely by a control box.

DRAWINGS—FIGURES

Figure 1:
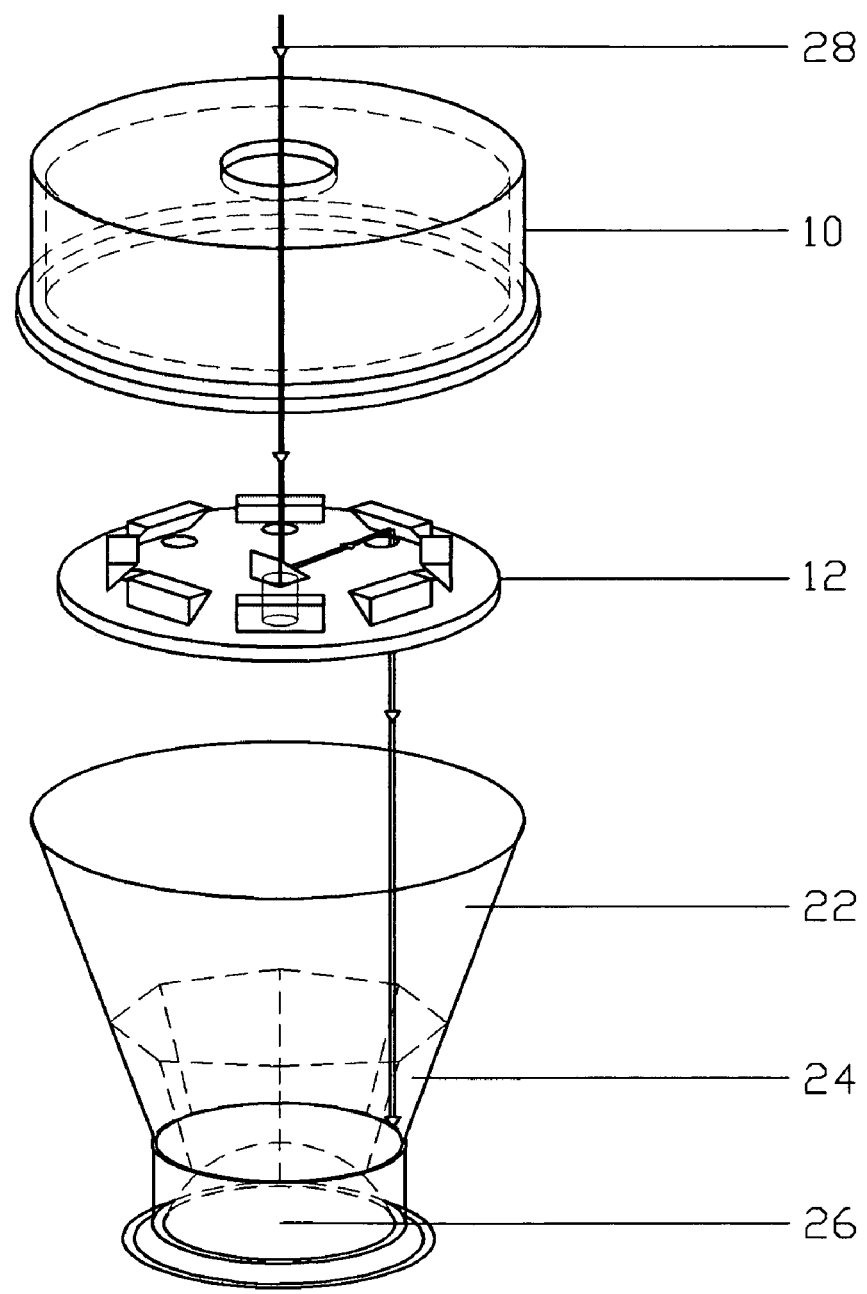
FIG. 1 shows an exploded view of the device from a lateral view. A ring of mirrors and a special lens are seen at the bottom of the instrument.

DRAWINGS—REFERENCE NUMBERS 10 external device casing
12 fenestrated disc
14 micromotor
16 holes associated with peripheral mirrors
18 mounted central reflecting mirror/prism
20 peripheral reflecting mirror/prisms
22 external contact lens housing
24 ring of mirrors for internal reflection
26 concave lens and hole
28 entering laser beam
30 control box
32 attachment cable

DETAILED DESCRIPTION—PREFERRED EMBODIMENT—FIGS. 1-4

Figure 2:
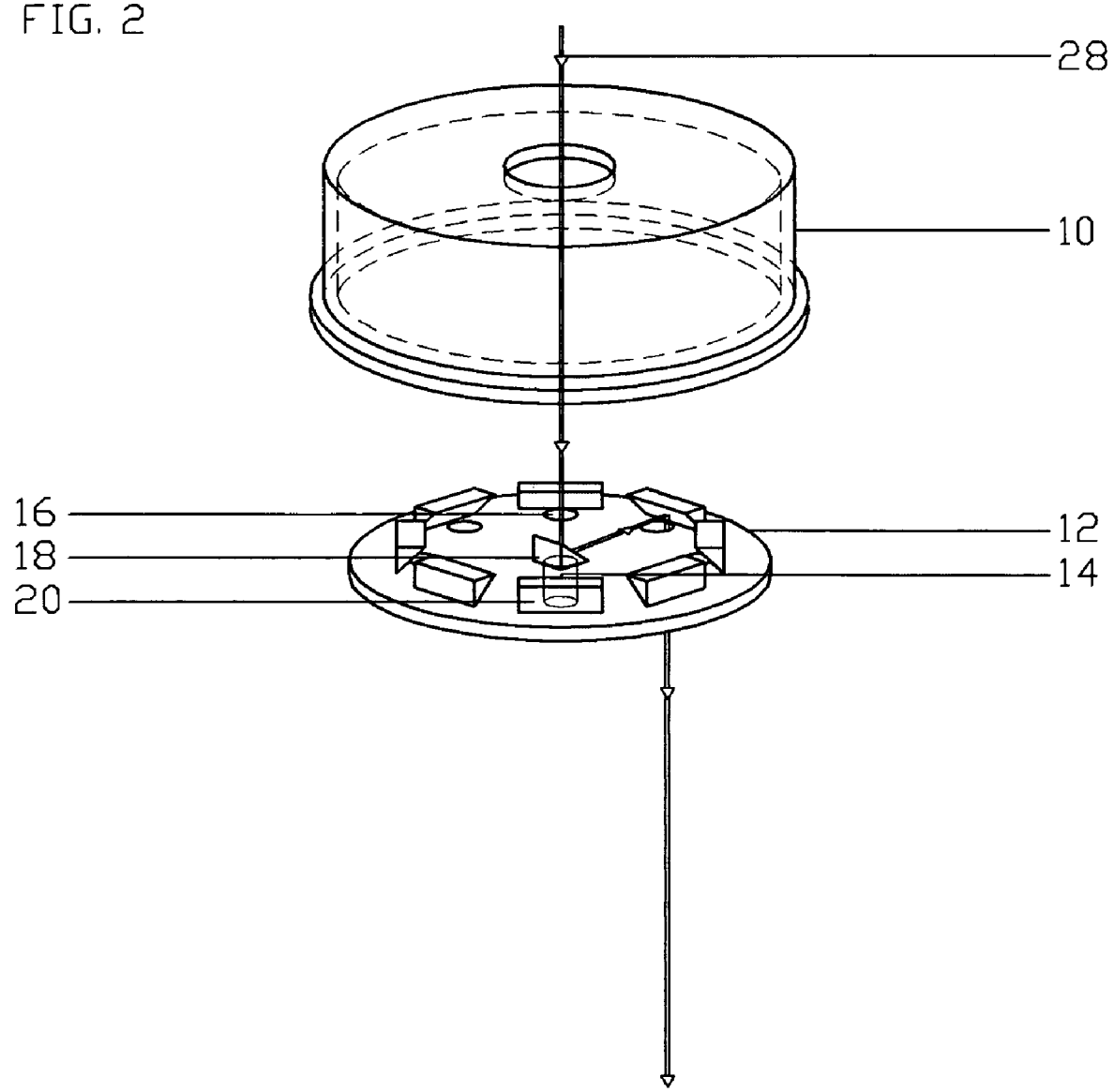
FIG. 2 shows the top of the fundus contact in side view with laser light redirected by the central mirror and subsequently diverted again by peripheral mirrors.
Figure 3:
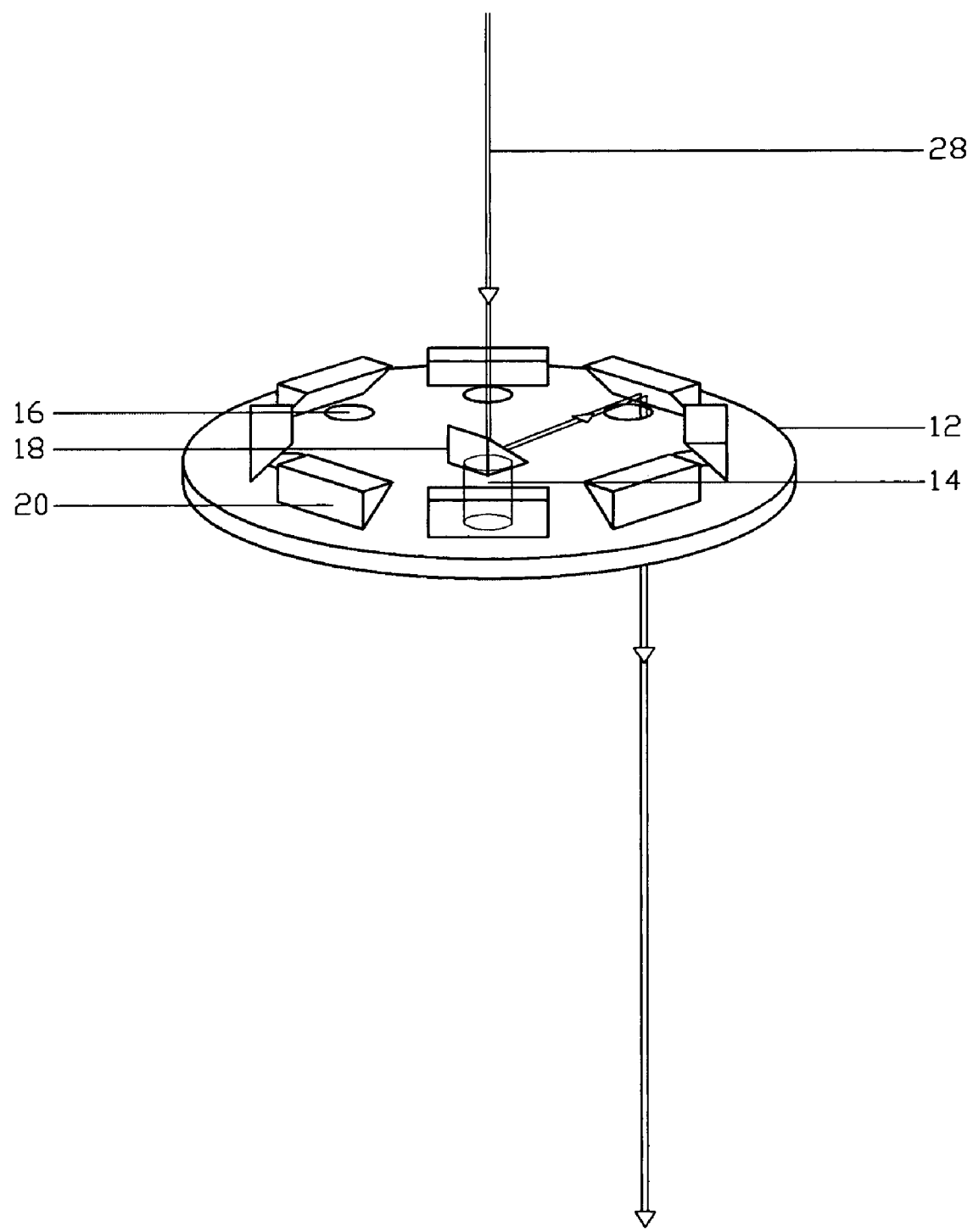
FIG. 3 shows the fenestrated disc mounted with mirrors or prisms and a micromotor.
Figure 4:
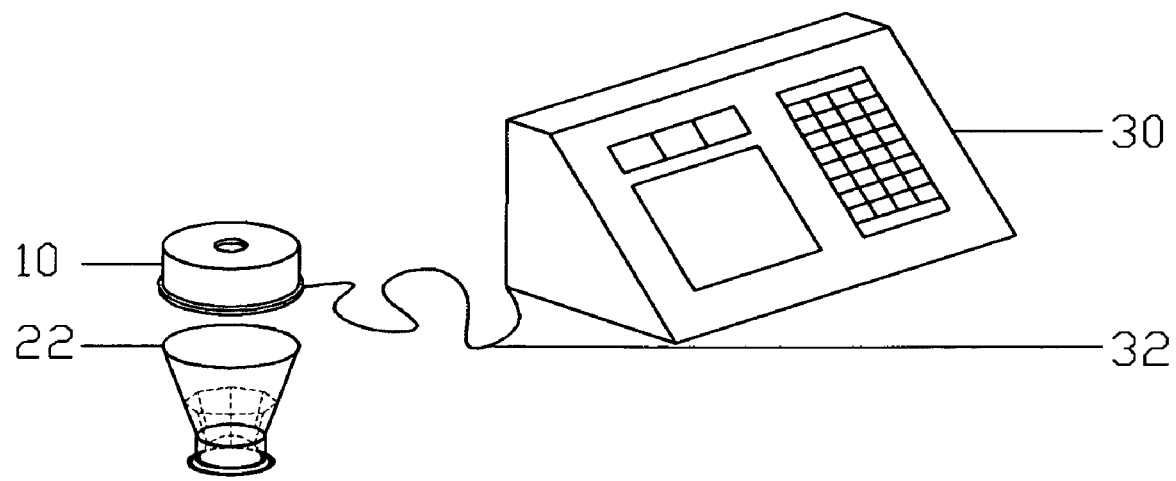
FIG. 4 shows the device connected to a control box.

The preferred embodiment of the invention is shown in FIGS. 1-4. The external housings 10 and 22 of the device are seen in a lateral exploded view in FIG. 1. Laser light 28 from a source is depicted entering the top of the invention. Initially the highly focused energy strikes the angled central mirror or prism that is mounted on a fenestrated disc 12. After reflection the light strikes one of the peripheral mirrors. Again diversion takes place and the energy is redirected to the ring of peripheral mirrors 24 arranged circumferentially toward the base of the instrument. Redirection of the beams ensues and the light passes through a lens 26 and a hole at the bottom of the fundus contact lens into the internal eye. FIG. 2 depicts the top of the invention in a lateral view with more detail. When the laser beam 28 strikes the central mirror 18 it is noted that micromotor 14 lies near the central reflecting surface. It gives the central mirror/prism rotary capacity such that beam diversion will strike each of the peripheral mirrors 20 arranged and mounted circumferentially on a disc 12. A fenestration 16 immediately adjacent to each peripheral mirror allows the energy to pass through the system unimpeded. FIG. 3 shows an enlarged side view of the central disc 12, holes 16, mirrors 18 and 20, micromotor 14 lying below the central mirror along with laser beam 28 passing through the system. FIG. 4 shows the entire fundus contact lens connected to a control box.

Operation—Preferred Embodiment—FIGS. 1,3,4

The method of using the device to perform panretinal laser photocoagulation (PRP) is consistent with known operator techniques in the current art. It is anticipated that a slit lamp biomicroscope and a laser will be used in conjunction with this delivery system. In this scenario the patient's cornea is usually anesthetized with topical drops. A coupling agent such as methylcellulose is then applied to the base of the fundus contact lens. The lens is then steadied and placed on the subject's eye. In the preferred embodiment the base of the fundus contact will have an arrangement of circumferential mirrors as delineated by Eisenberg (2004) in U.S. patent application Ser. No. 11/024,308. At that juncture the treating surgeon sets variable laser parameters such as power, spot size, pulse duration, and wavelength. In addition the physician will choose, via a control box 30 (FIG. 4), the speed of central mirror rotation located within the panretinal laser fundus contact lens. It is anticipated that in the preferred manifestation a large diameter laser beam will be employed. Nothing, however, inhibits the device from being used with a varying range of beam sizes. Furthermore, nothing prevents the instrument from being utilized with laser wavelengths outside the conventional (400-700 nm) range.

With the preferred embodiment an examiner will be able to temporarily rotate the central disc 12 (FIG. 1) of the invention to prevent it from blocking the physician's view of the internal eye. Once the fundus contact is present on the patient's eye the posterior lens in the device allows the examiner to center the patient's macula in the primary position. Thereafter, the peripheral mirrors 24 (FIG. 1) in a ring configuration located in the posterior aspect of the instrument can serve to image and focus the peripheral retina. At that juncture the disc 12 (FIG. 1) mounted with mirrors/prisms can be returned to its functional position so that treatment can be started. Activating a trigger switch will then send laser pulses to the central mirror 18 (FIG. 3) close to micromotor 14 (FIG. 3) The laser beam will then be redirected to a peripheral mirror 20 (FIG. 3). After striking this mirror it will again undergo reflection and a directional change. The light will exit the disc through a fenestration 16 (FIG. 3) located beneath each peripheral reflecting device. Upon leaving the disc platform bundles of laser energy will then hit the corresponding mirrors 24 (FIG. 1) within the ring system at the bottom of the fundus contact. Subsequently, they will exit the device through a lens and hole 26 (FIG. 1) at the base of the invention. At that point the energy will be directed to its final target in the internal eye (retinal/choroid). The entire process from the incident beam to the exit beam will be repeated in an automated fashion. Micromotor 14 (FIG. 3) will serve to rotate the mounted central mirror 18. As the central reflecting device moves it will send laser energy to a different peripheral mirror arranged on disc 12 (FIG. 1). Thus, the light will subsequently be diverted to a different mirror at the bottom of the device. Hence, the anatomical target in the retina will change with each fixed, angular rotation of the central mirror.

In this fashion a ring of laser applications will be automatically placed within the eye without manually aiming each application. This methodology will not only speed the process of panretinal photocoagulation it will reduce operator errors. In addition, it will reduce the coordination necessary to perform treatment. If a broad laser beam diameter is used for the treatment a complete course of therapy might be reduced to seconds.

Description—Alternative Embodiments

A number of possibilities exist for alternative embodiments of this invention. First, the shape of the external housing of the device in the preferred embodiment is a truncated cone. This is in conformity with most of the current fundus contacts that are commercially available at the present time. However, nothing prevents the device from taking another conformation. It could, for example, easily fit inside a cylindrical body. Second, the mechanism to move the central disc with mounted mirrors so as to allow an examiner to focus on the posterior segment of the eye, has a number of possibilities. In the preferred model the disc is connected to a rod or a wheel that allows the treating surgeon to manually rotate the platform of mirrors. However, this could be achieved electronically without deviating from the spirit of the invention. Furthermore, the internal disc suspending the reflective elements could be hinged to the fundus contact body and swing in and out of place, manually or electronically, at the command of the treating surgeon. Third, the circumferential mirror system at the base of the invention (the last reflective element in the invention prior to the laser light entering the eye) could have a variable number of mirrors/prisms. While the preferred embodiment is drawn with eight the invention could be made six, twelve, or any other number. In addition, the shape of these reflective elements is variable. They might be made as rectangular, semicircular, truncated cones, or triangular. The specific shape of the mirrors is not central to the thesis of the device. Fourth, the regulation of the instrument is depicted with a cable connection to a control box. However, a wireless control might easily be used. Or the electrical circuitry of the laser and biomicroscope might be integrated so as to control the invention. Fifth, one skilled in the art might construct an instrument mimicking the current invention by arranging multiple barrels of laser beams designed to discharge in successive fashion. If the tubes were arranged in a circular fashion and the mirrors of the fundus contact were designed to receive the laser delivery the net result would be analogous to the current device. The successive firing of each laser source or the simultaneous discharges from all would produce a ring of photocoagulation consistent with the current invention. Finally, the position of the micromotor in the device is optional. While the current embodiment is depicted with the micromotor lying below the central reflecting mirror it can easily lie elsewhere. For example, the small motor might occupy a space lateral to the central mirror. It could protrude from the body of the contact lens in an alternative embodiment. In this arrangement it would be connected to the central mirror via a tube or gearing system that would enable it to rotate the central reflecting device. Simultaneously, an examiner might be able to rotate the micromotor and effectuate a repositioning of the central disc with mounted mirrors. From the foregoing discussion it is evident that the exact placement of the micromotor in the device is not critical to the operating principle of the instrument.

Advantages

From the previous description a number of the advantages of our invention become evident:
a) The time to complete panretinal laser photocoagulation will be shortened. A rotating laser beam will help automate the treatment process.
b) The device will reduce the user coordination involved with the current treatment strategy since the operator will not have to manually aim and trigger each individual application.
c) This fundus contact lens will be relatively small and easily portable. Thus, automating a treatment will not require a large hardware platform of heavy and expensive equipment.
d) Aiming errors by the treating surgeon will be diminished. The invention will promote the automatic delivery of laser energy to the interior eye without the manual use of a micromanipulator.
e) This treatment adaptation will reduce the patient pain associated with panretinal laser therapy. If used either in conjunction with a broad beam laser or with decreased pulse durations the net energy delivered to the retina will be less. This, along with faster delivery times, will minimize patient discomfort.
f) Enhanced safety will result from the instrument. Speeding and automating the process of panretinal laser treatment will result in less fatigue for the patient and the surgeon. Furthermore, it will cut the incidence of misdirected laser energy due to operator errors.
g) The complications of panretinal laser surgery will be reduced. If less energy is delivered to the eye the side effects of current treatments should be less. This would include untoward results such as visual field contraction, contrast sensitivity reduction, and nyctalopia. It is even possible macular edema might be lessened by our invention.
h) The apparatus will assist in automating a process which is heavily burdened with manual input.

CONCLUSIONS, RAMIFICATIONS, SCOPE

Thus, the reader will see that a specialized fundus contact lens can be used to provide a faster and safer method for performing panretinal laser photocoagulation. This is accomplished by diverting laser light energy within an instrument that is held on the eye during treatment. By mechanically rotating a central mirror that receives laser energy the light can be redirected to mounted peripheral mirrors/prisms which divert the energy in a circular configuration. In this fashion an annular ring of photocoagulation can be delivered to the internal eye. The effects of the invention will be to speed the process of treatment, to reduce patient pain, to reduce operator fatigue, to minimize aiming errors, and to minimize the complications of the procedure.

The above description contains many specificities and these should not be construed as limitations on the scope of the invention. Instead they should be seen as exemplifications of the preferred embodiment. Many variations are possible aside from the ones previously discussed. For example, a rod or cylindrical attachment might extend from the body of the contact lens and connect to the mirror mounted disc. This might facilitate rotating or moving the reflective platform so that the examiner could use the posterior lens in the contact to view the internal eye. Alternatively, the plate of mirrors might exist in a configuration that allows it to be removed entirely from the interior of the fundus contact. Then subsequent reinsertion, after checking the patient's eye position, would allow therapy to proceed.

It is apparent that the scope of the invention should be determined by the appended claims and their equivalents.

We claim:
1. An ophthalmic fundus contact lens device for delivering laser photocoagulation energy comprising:
 (a) a body and anterior surface for positioning the device proximate to the eye of a patient,
 (b) a disc mounted with central and peripheral reflecting mirrors/prisms to redirect laser energy,
 (c) a micromotor designed to connect and translate rotational force to the central mirror of said disc,
 (d) a plurality of mirrors or prisms installed internally in an annular fashion within said body,
 (e) a lens encased for viewing the posterior segment of the ocular anatomy,
 (f) a control apparatus to coordinate the sequential firing of the laser with the rotation of the central mirror, whereby said assembly will function to deliver laser energy to the eye fundus.

2. The fundus contact lens in claim 1 wherein said body is a truncated cone.

3. The fundus contact lens in claim 1 wherein said plurality of posterior mirrors/prisms circumscribing a circle are eight in number and contiguous.

4. The fundus contact lens in claim 1 wherein said body contains a posterior flange to facilitate insertion and stabilization under the eyelids.

5. The fundus contact lens in claim 1 wherein the posterior end of said body has a radius of curvature approximating the human cornea.

6. The fundus contact lens in claim 1 wherein said body is composed of plastic.

7. The fundus contact lens in claim 1 wherein said said lens for viewing the posterior segment is concave.

8. The fundus contact lens in claim 1 wherein the micromotor is positioned below the central rotating mirror.

9. The fundus contact lens in claim 1 wherein the micromotor is positioned lateral to the mounted central mirror.

10. The fundus contact lens in claim 1 wherein the mounted disc platform is moveable.

11. The fundus contact lens in claim 1 wherein the micromotor is regulated by a control box.

* * * * *